(12) United States Patent
Bond

(10) Patent No.: US 8,142,834 B2
(45) Date of Patent: Mar. 27, 2012

(54) FINGERPRINT DETECTION

(75) Inventor: John Bond, Northampton (GB)

(73) Assignee: Northamptonshire Police Authority (GB)

( * ) Notice: Subject to any disclaimer, the term of this patent is extended or adjusted under 35 U.S.C. 154(b) by 623 days.

(21) Appl. No.: 12/300,445

(22) PCT Filed: Apr. 10, 2008

(86) PCT No.: PCT/GB2008/001261
§ 371 (c)(1),
(2), (4) Date: Nov. 11, 2008

(87) PCT Pub. No.: WO2008/125818
PCT Pub. Date: Oct. 23, 2008

(65) Prior Publication Data
US 2009/0185725 A1    Jul. 23, 2009

(30) Foreign Application Priority Data

Apr. 12, 2007 (GB) .................................. 0707058.4
Jan. 8, 2008 (GB) .................................. 0800244.6

(51) Int. Cl.
*A61B 5/117* (2006.01)
*G03G 13/08* (2006.01)
(52) U.S. Cl. .................................. 427/1; 427/7; 430/48
(58) Field of Classification Search .................... 427/1, 7
See application file for complete search history.

(56) References Cited

U.S. PATENT DOCUMENTS

| | | | |
|---|---|---|---|
| 3,924,568 A * | 12/1975 | Jeromin | ........................ 399/291 |
| 4,258,073 A * | 3/1981 | Payne | ............................... 427/1 |
| 5,079,029 A | 1/1992 | Saunders | |
| 5,801,729 A * | 9/1998 | Kitamura et al. | ................ 347/55 |
| 6,592,929 B1 | 7/2003 | Berka | |
| 2006/0063085 A1* | 3/2006 | Lee et al. | .................. 430/108.22 |

FOREIGN PATENT DOCUMENTS

| | | |
|---|---|---|
| GB | 1500592 A1 | 2/1978 |
| GB | 2015430 A | 9/1979 |

OTHER PUBLICATIONS

Schanen et al., Electric field investigation in high voltage power modules using finite element simulations and partial discharge measurements, IEEE, 2003, p. 1000-1005.*
Williams et al., Latent fingermark visualisation using a scanning Kelvin probe, Forensic Science International, 167, Oct. 4, 2006, 102-109.*
GL Thomas "The physics of fingerprints and their detection", J. Physics, vol. 11, 1978, pp. 722-731.
Search Report for Application No. GB 0707058.4, Jul. 30, 2007.
International Search Report for International Application No. PCT/GB2008/001261, Aug. 20, 2008.

* cited by examiner

*Primary Examiner* — Michael Cleveland
*Assistant Examiner* — Francisco Tschen
(74) *Attorney, Agent, or Firm* — Caesar, Rivise, Bernstein, Cohen & Pokotilow, Ltd.

(57) ABSTRACT

A method of and apparatus (2) for locating and detecting a fingerprint deposited on a surface (10), the method comprising setting up an electric field such that a differential charge density is produced coincident with the location of a fingerprint deposited on the surface. By deploying a conductive powder or other detection element selectively attractable to the surface (10) coincident with the differential charge density in the region of the fingerprint deposit a fingerprint deposited on the surface (10) is located and detected.

9 Claims, 4 Drawing Sheets

FINGERPRINT DETECTION

CROSS-REFERENCE TO RELATED APPLICATIONS

This national stage application claims the benefit under 35 U.S.C. §371 of International Application No. PCT/GB2008/001261 filed on Apr. 10, 2008, entitled FINGERPRINT DETECTION, which in turn takes its priority from Great Britain Application No. 07070584 filed on Apr. 12, 2007 and Great Britain Application No. 0800244.6 filed on Jan. 8, 2008, and all of whose entire disclosures are incorporated by reference herein.

BACKGROUND OF THE INVENTION

1. Field of Invention

The invention relates generally, but not exclusively, to an apparatus for and method of detecting fingerprints. More specifically, but not exclusively, the invention relates to a method of and apparatus for detecting fingerprints by creating a differential charge density with respect to the surrounding surface in the region of a deposited fingerprint.

2. Description of Related Art

It is widely known to locate and detect fingerprints deposited on metal or other surfaces using chemical reactions with either the eccrine (amino acid) and/or sebaceous (fatty acid) content of a fingerprint residue. Other methods of detecting latent fingerprints involve using the fingerprint residue as an insulator against electrochemical or reduction/oxidation (redox) reactions. Such methods are not usually suitable when the surface on which the fingerprint is deposited has become wetted (removing the aqueous eccrine content) or damaged (removing the sebaceous content). A surface can become wetted, or damaged by weathering or cleaning, for example.

Another known technique measures the difference in electrical potential between a metal substrate on which a fingerprint has been deposited and a metal probe. The technique exploits a discovery made by Lord Kelvin in the nineteenth century, which is that different metals, connected electrically, have a potential difference between them determined by the work function of the metals. The work function of a particular metal is a measure of the ease with which an electron can leave the surface of the metal. The chemicals found in a fingerprint deposit cause corrosion of a metallic surface. The work function of a metal changes where it has been corroded by a fingerprint. Therefore a work-function based technique relies on measuring the differences in work function across the whole of a surface of a metal where it is suspected a fingerprint has been deposited. Clearly, this can be a time consuming and haphazard process.

It is desirable to be able to locate and identify fingerprints deposited on a wide variety of surfaces even when such surfaces have been exposed to outdoor conditions or have been cleaned, for example by persons trying to hide their actions. The present invention seeks to avoid or mitigate at least one or more of the problems of the prior art by providing an apparatus for and method of detecting latent fingerprints which is suitable for use on a wide variety of materials, for example where the fingerprint residue has been diminished.

BRIEF SUMMARY OF THE INVENTION

According to a first aspect, the invention provides a method of and/or apparatus for locating and detecting at least part of a fingerprint deposited on a surface, comprising means for setting up an electric field such that a differential charge density is produced coincident the location of at least part of a fingerprint deposited on the surface; and a detection element, wherein the detection element is selectively attractable to or repellable from the surface coincident the differential charge density in the region of the fingerprint deposit, such that at least part of a fingerprint deposited on the surface can be located and detected.

Preferably, the electric field is set up such that the charge density of the surface at the fingerprint deposit is lower than the charge density of the surrounding region of the surface. The electric field may be set up such that there is a potential difference across the surface. The electric field may be from, say, 0 to 5 KV, say from 0 to 3 kV, for example in the order of 2.5 kV.

Additionally or alternatively, the detection element may comprise a conductive powder, for example a black conducting powder, which may be applied to the surface, for example such that in the area or location of the deposited fingerprint or part thereof, the conductive powder may be selectively attracted to or repelled from the deposited fingerprint or part thereof, thereby providing a visualisation of the deposited fingerprint or part thereof.

The detection element may also comprise ceramic beads coated in a or the conductive powder, such that in the location of the deposited fingerprint or part thereof, at least a part of a or the conductive powder may be removed from the ceramic beads and may be attracted to or repelled from the fingerprint deposit, thereby providing a visualisation of the deposited fingerprint or part thereof. The detection element may comprise an aerosol spray, which may comprise a powder, say a conductive powder which in the area or location of the fingerprint or part thereof, may be attracted to or repelled from the deposited fingerprint or part thereof, for example thereby providing a visualisation of the deposited fingerprint or part thereof.

A second aspect of the invention provides apparatus for applying a potential across an irregularly shaped object, the apparatus comprising a first clamp means and a support surface, between which the article is retainable, and a pair of contacts for contacting the article held between the clamp and support surface, at least one of the contacts comprising reciprocable portions to accommodate different portions of said object.

Preferably one or both of the clamp means and the support surface are reciprocable towards and away from one another. Preferably one or both of the clamp means and the support surface are rotatable.

At least one of the contacts preferably comprises a spring to provide said reciprocable portion. Additionally or alternatively, other resilient means may be provided.

BRIEF DESCRIPTION OF SEVERAL VIEWS OF THE DRAWINGS

Exemplary embodiments of the invention will now be described by way of example only and with reference to the accompanying drawings in which.

The exemplary method described and depicted herein involves applying an electrical potential of the order of 2.5 kV to a metallic sample upon which a fingerprint has been deposited. The applied potential difference creates a charge density at the surface of the sample material. At the place where a fingerprint has been deposited (before it was damaged or wetted), the charge density is different relative to the charge density of the surrounding area of the sample surface. This is due to the effect that the chemicals comprised in the fingerprint deposit have had on the metallic sample; that is, a corrosion of the metallic surface. A conducting powder is then applied, using at least one of two methods which are described below, the conductive powder being attracted to and adhering to the fingerprint.

DETAILED DESCRIPTION OF THE INVENTION

Figure 1:
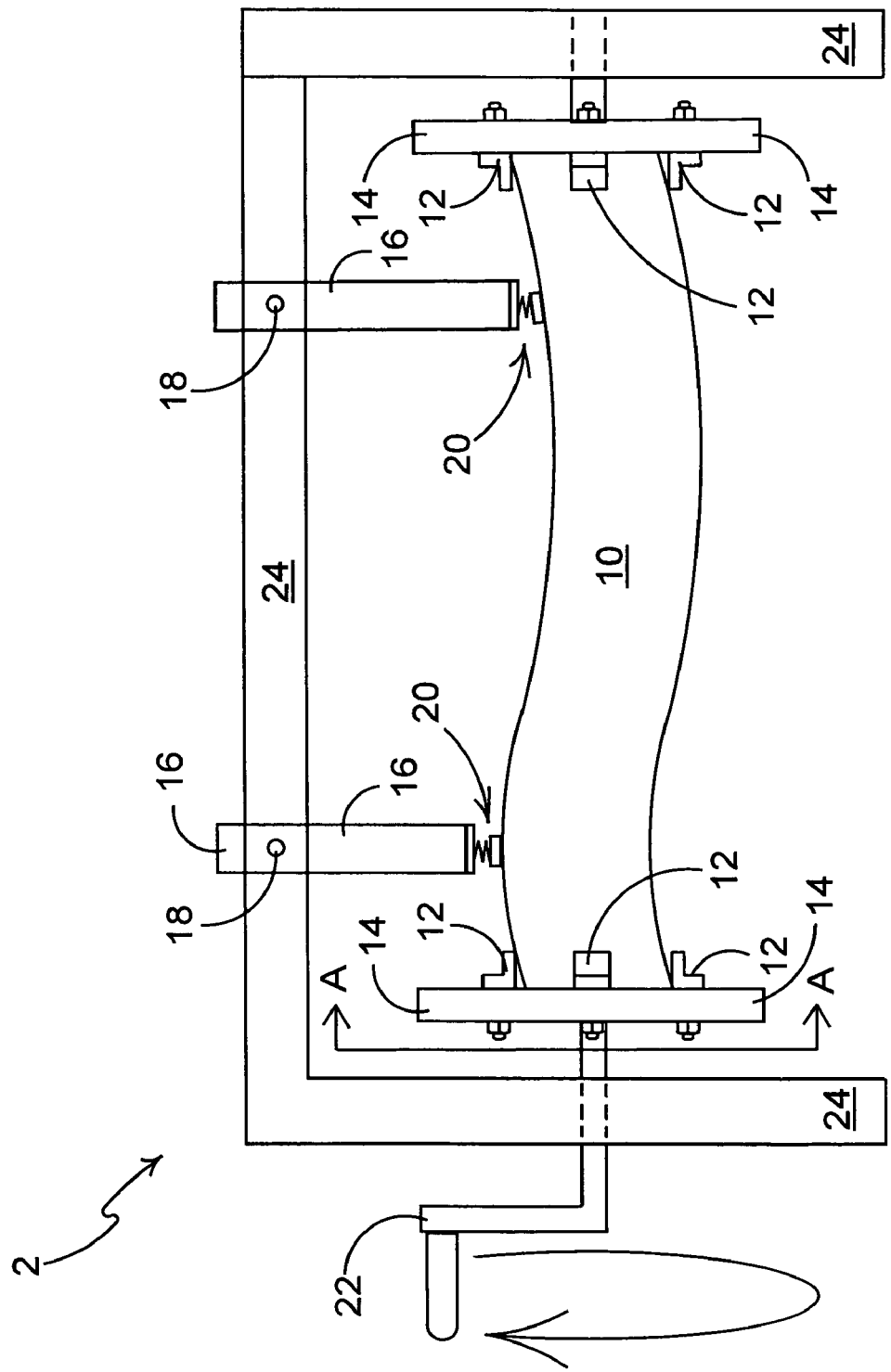
FIG. 1 shows a diagram of an apparatus suitable for detecting at least part of a latent fingerprint according to one embodiment of the present invention.

FIG. 1 shows a diagram of an apparatus 2 for detecting a latent fingerprint 50 (not shown in FIG. 1) on a sample material 10 clamped within the apparatus 2. The apparatus 2 includes a supporting frame 24, a pair of circular plates or disks 14 rotatably mounted to opposing portions of the supporting frame 24, a cranked handle 22 extending from an external surface of one of the circular plates 14 and through the frame 24, a pair of rods 16 and a high voltage unit (not shown).

Figure 2:
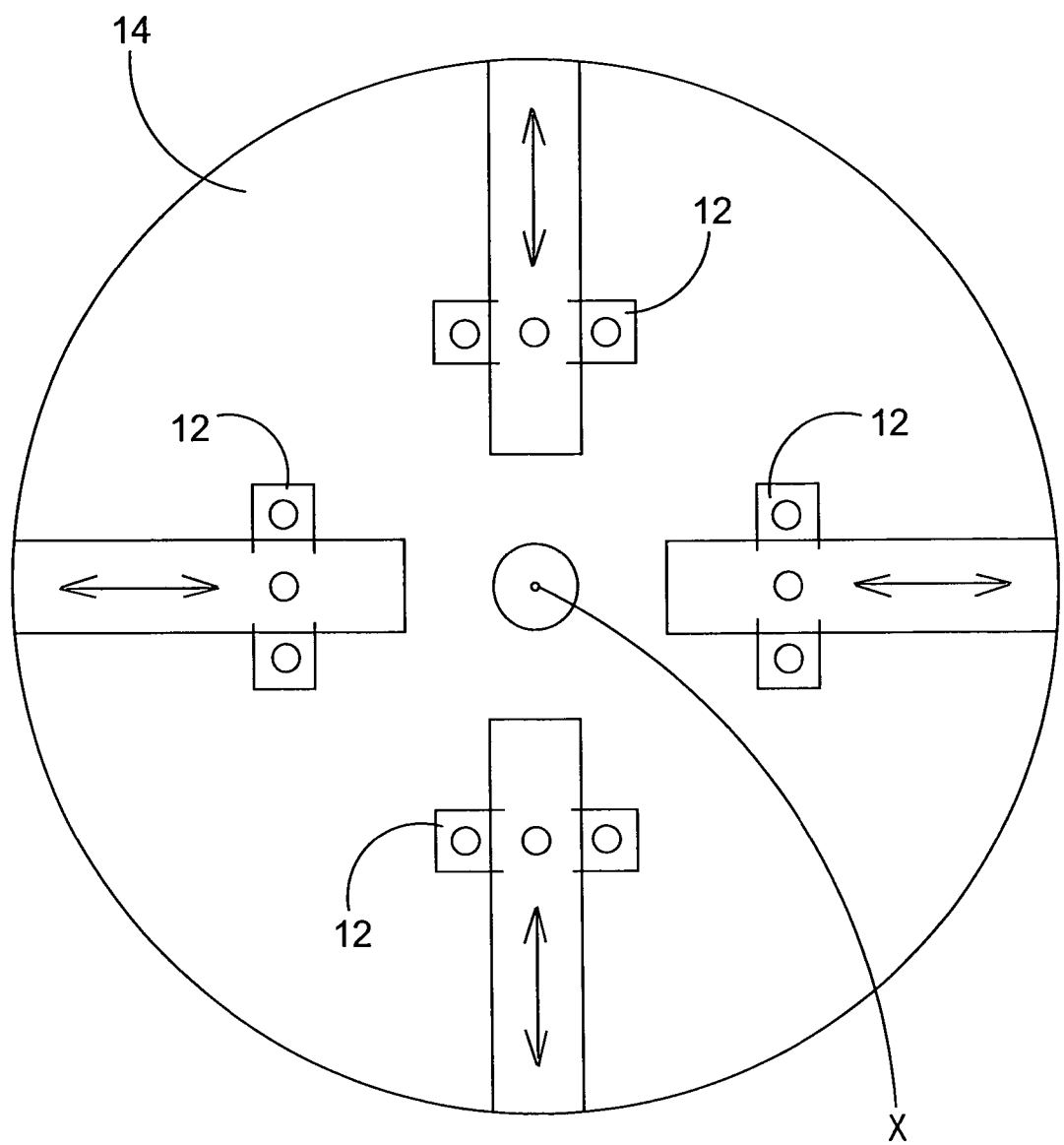
FIG. 2 shows a view along line AA of the apparatus of FIG. 1.
Figure 4:
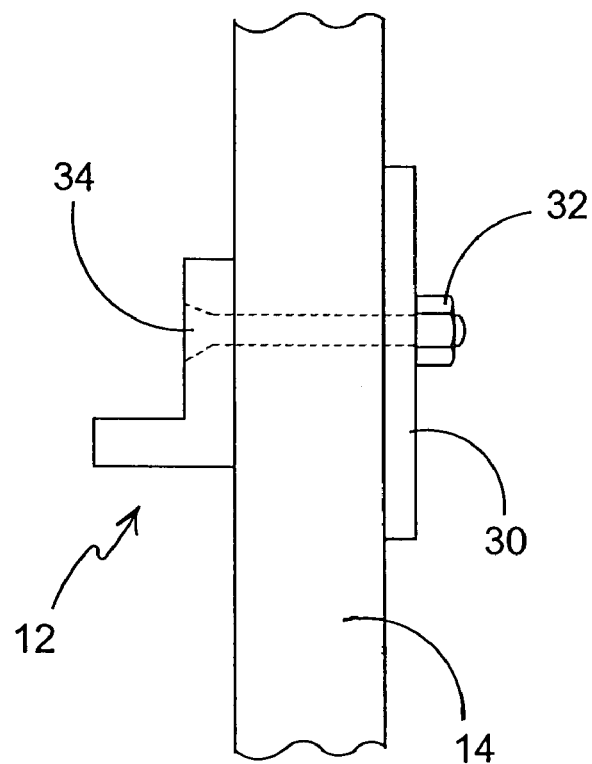
FIG. 4 shows a more detailed diagram of the clamping mechanism of FIG. 1.

Each circular plate 14 includes four clamping mechanisms 12, shown more clearly in FIGS. 2 and 4, which are fully adjustable radially inwardly or outwardly across the circular plate 14 until contact is made with the sample material 10. Each clamping mechanism 12 is adjustably mounted to the circular plate 14 by a clamping plate 30, which is attached via a nut and bolt arrangement 32 to a clamping member 34. The clamping mechanism 12 is fully adjustable across the circular plate so as to be able to clamp sample material 10 of varying sizes (not shown) between the clamps 12.

The circular plates 14 are rotatable about a principal axis of rotation X using the handle 22 or other suitable mechanism. The clamped sample material 10 is, in this embodiment, an irregularly shaped brass object which is believed to have a fingerprint deposited thereon by an unknown person.

Figure 3:
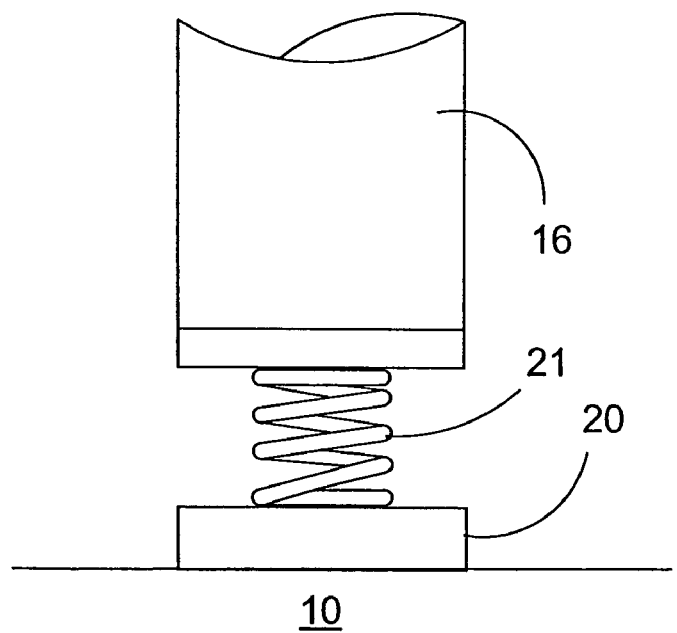
FIG. 3 shows a more detailed diagram of the brass rod and bronze plunger contact arrangement of FIG. 1.

The rods 16 are made of brass in this embodiment, although any suitable conductive material may be used. As shown more clearly in FIG. 3, each rod 16 includes a plunger contact 20 which is mounted to an end of the rod 16 by a spring 21 in this embodiment, although any suitable resilient biasing means could be used. The rods 16 are adjustably mounted to the frame 24, say by grub screws 18, such that they extend inwardly of the apparatus 2 toward the sample material 10 in use. This arrangement enables the rods 16 to be adjusted to ensure that the plunger contact 20 is in contact, in use, with the sample material 10. The spring 21 enables the plunger contact 20 to adjust to and follow the contours of irregularly shaped surfaces of a sample material 10 whilst it is rotated.

Electric potential is provided, in use, by the high voltage unit (not shown), based around a Brandenburg 3590 series high voltage module. The unit enables the generation of a continuously variable potential from 0-2.5 kV.

Other high voltage modules may be used which generate different potentials.

An electrical potential of the order of 2.5 kV is applied through the conductive brass rods 16. It has been observed that the higher the voltage the better the observed affect and therefore many voltages other than 2.5 kV will create a differential charge density sufficient to enable a latent fingerprint to be detected and identified. It should be clear to a person skilled in the art that the present invention is not limited solely to the application of a potential voltage of 2.5 kV and that lower or higher potentials may be applied.

It will also be clear to a person skilled in the art that any suitable means of clamping the sample material securely so that it can be rotated or tilted when being examined can be used and that the present invention is not limited to only the mechanical arrangement of clamps and plates as described with reference to FIGS. 1 through 4. For example two, three or more clamps 12 and/or other types of clamps (not shown) can be used.

The apparatus 2 may also be used to enhance fingerprints on non-metallic (i.e. insulating) sample materials 10. Non-metallic objects are clamped or clampable in the same way as described with reference to FIGS. 1 through 4 above, although the rods 16 and plunger contacts 20 are removed. An electric field is then applied in the vicinity of the non-metallic sample material 10 by means of two metal, for example brass, plates (not shown) positioned on either side of the sample material 10 and charged with a potential of opposing polarities. It should be noted that if the substrate containing the residue also polarizes, then the differential charge density set up may not distinguish as well between the fingerprint trace where the fingerprint residue reacted with the sample and the surrounding area. Nevertheless, fingerprint traces may still be resolved.

When a latent fingerprint needs to be located and detected on the surface of a sample material 10, using the apparatus as described above, at least two methods may be used to apply a conducting powder.

The first method requires the introduction to the sample material 10 of ceramic spherical beads, for example of approximately 10 microns in diameter, which are coated in a fine granular (~2 micron) black conducting powder. The ceramic spherical beads are then rolled over the surface of the sample material 10 (aided by the turning thereof). The coated ceramic spherical beads are known in the art and are commercially available.

The ceramic spherical beads act as a carrier for the conducting powder onto the sample material 10. The beads do not themselves adhere to the sample material 10, the conducting powder on them does. The ceramic beads are spherical so they can easily move across the surface of the sample material 10.

The conducting powder is charged when the ceramic spherical beads come into contact with the charged sample material 10. The beads roll across the surface of the sample material 10 and the conducting powder acquires the potential of the sample material 10. When fingerprint residue is reached, these areas have a potential difference relative to the surrounding area and the conducting powder is attracted to or repelled from this area due to electrostatic effects.

On a metallic sample material 10, the grains attract a charge equal to the charge of the metallic sample material 10. On contact with a latent fingerprint, the lower potential of the fingerprint residue/metal corrosion attracts the grains from the beads and onto that part of the metal coincident the fingerprint residue/corrosion.

Figure 5:
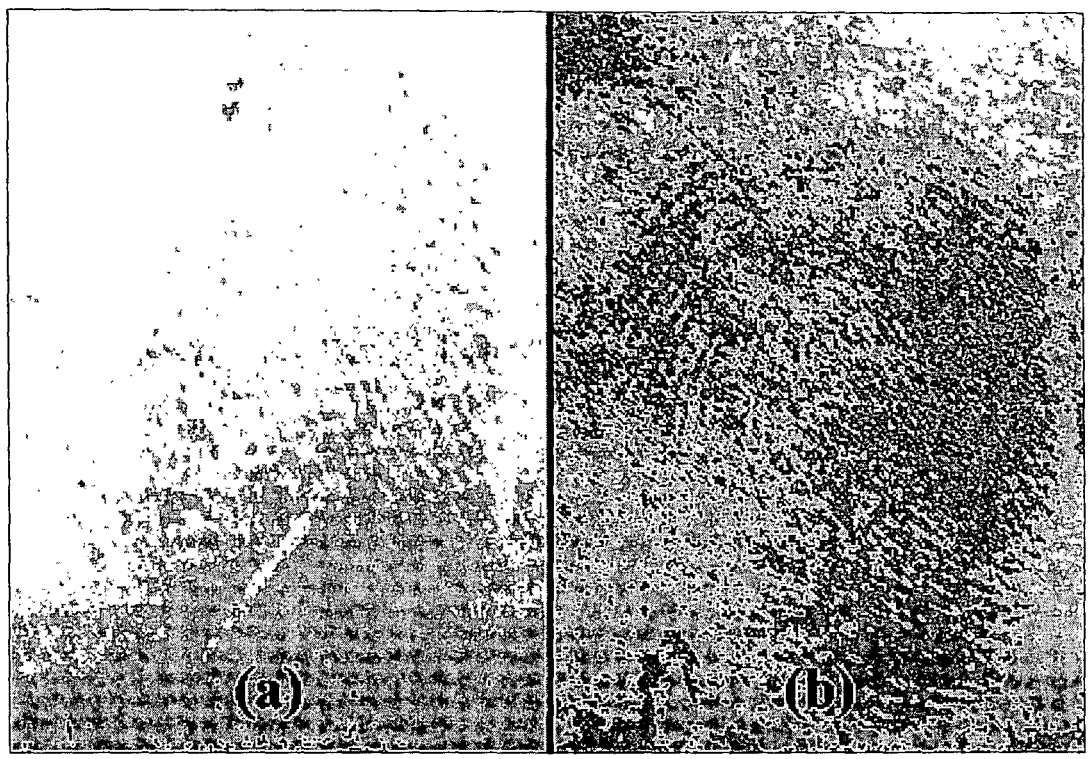
FIG. 5 shows ridge detail development for a fingerprint deposited on brass, five days after deposition. (a) shows the degree of redox corrosion visible after washing in water, acetone and then water and (b) shows the same fingerprint after subsequent electrostatic enhancement.

In FIG. 5 a brass sample surface is illustrated onto which a fingerprint has been deposited. The sample surface has been washed in water, acetone and then water again. The image of FIG. 5 (*a*) has been taken five days after deposition of the latent print and FIG. 5(b) shows the ridge detail development of the same fingerprint after subsequent electrostatic enhancement using the method and apparatus of the present invention. It is shown that after using electrostatic enhancement, the fingerprint can be detected and identified whereas before, the fingerprint could not be seen.

After electrostatic treatment, the conducting powder is generally vulnerable to disturbance after the electric charge has been removed. By heating the sample material 10 after treatment to a temperature of, for example 150° C., the powder will bind to the sample material 10, thereby producing a more durable sample.

On a non-metallic sample material 10, the applied electric field will polarize components within the fingerprint residue encouraging (uncharged) grains to be attracted to (or repelled from) the charge on the residue.

The second method usually involves the spraying of fine granular conducting powder onto the sample material 10 by means of say an aerosol. The aerosol nozzle is charged with a potential of opposite polarity to the sample material 10. On the metallic sample material 10, the charged conducting powder would be attracted to the lower potential on the sample material 10 either co-incident with the fingerprint residue/corrosion or the surrounding area such that either an inverted or normal trace of the fingerprint is obtained.

On a non-metallic sample material 10, the charged conducting powder is attracted to the polarized charge on the residue of opposite polarity to the charge on the powder.

It will be appreciated that the method and apparatus of the invention allows investigation of a substrate to determine whether or not a fingerprint or part thereof is present. The method is rapid insofar as the whole of the substrate need not be examined in minute detail, for example by setting up an examination array comprising a plurality of points for investigation.

Whilst the inventors do not wish to be limited by any theory, the mechanism for this process, when used on metallic materials, is thought to be a consequence of the corrosion on the metal surface that leads to both impurities and lattice imperfections, which will have the affect of locally increasing the resistivity of the metal at the site of the corrosion. If a potential is applied to the metal sample 10 then, under electrostatic conditions, the charge will move entirely to the outer surface with the electric field inside the metal being zero. Areas of corrosion with increased resistivity will behave more like a dielectric and the charge density in these areas ($\sigma'$) will be less than the charge density at other parts of the surface ($\sigma$). Using Gauss' Theorem, both the electric field and potential at a given point above the disk will be less above a corroded area.

More specifically, in a section through a metal disk under electrostatic equilibrium, where $\alpha$ represents a Gaussian surface drawn partly through the surface of the metal that has a surface area in the plane parallel to the exterior surface of the metal of A, the Gaussian surface contains a charge $$q = \sigma \cdot A.$$

From Gauss' law, $$q = \epsilon_0 \oint \underline{E} \cdot d\underline{A}$$

where $\epsilon_0$=permittivity of free space and, at all points on the Gaussian surface E and dA have the same direction.

Assuming that E has the same magnitude at all points on the Gaussian surface then $$q = \epsilon_0 E \oint dA = \epsilon_0 E \cdot A$$

and therefore $$E = q/\epsilon_0 A$$

By the same derivation, if the Gaussian surface $\alpha'$ (taken or drawn through a corroded area) has the same surface area A then $$q' = \epsilon_0 E' \oint dA = \epsilon_0 E' \cdot A$$

and therefore $$E' = q'/\epsilon_0 A$$

As q'<q then it follows that E'<E.

Further, as the potential difference ($\Delta v$) between two points separated by a distance d is given by $$\Delta v = \int_0^d E \cdot ds$$

the potential at a given point above Gaussian surface $\alpha'$ will be less than the potential above $\alpha$.

It will be appreciated by those skilled in the art that various changes may be made without departing from the scope of the present invention, for example, the size and shape of the frame and clamping arms and clamping mechanism may be adjusted to accommodate sample materials of differing size or shape. It is also envisaged that other methods of applying the conducting powder would work equally well and would still produce the desired effect.

Also, the ceramic beads need not be used. For example a conducting powder may be applied by other means, such as dusting.

It will also be understood by the skilled addressee that a detection element may be configured to be attracted to the area where the fingerprint is not or to be repelled from the area where the fingerprint, or part thereof, is deposited.

The conducting powder may be any size, for example 10 microns. The metallic material may be for example, copper, steel, aluminium, brass (as described above) or any other suitable metallic material.

The circular plates 14 may also be movable toward and away from one another to accommodate different sized and shaped articles.

The method need not be practiced on an article isolated from its environment. In particular, the method may be practiced on an article in situ. For example, a potential and the detection element may applied directly to the article in situ.

What is claimed is:

1. A method of detecting a latent fingerprint deposited on a surface, by detecting corrosion caused by the fingerprint, the method comprising applying an electrical potential across a metallic substrate such that a differential charge density is produced coincident the location of at least a partial, part or whole latent fingerprint deposited on a surface of the metallic substrate and deploying a detection element to selectively attract to, or repel from, the surface coincident, or selectively attract to or repel from the area non-coincident with the surface corresponding to the at least a partial, part or whole latent fingerprint deposited on the surface, such that the at least partial, part or whole latent fingerprint can be located and detected.

2. A method according to claim 1, wherein applying an electrical potential across the metallic substrate further comprises providing first and second contacts with the metallic substrate, wherein the first and second contacts are connected to a high voltage module to provide an electrical circuit.

3. A method according to claim 1, comprising establishing a lower charge density at the surface coincident the at least a partial, part or whole latent fingerprint than the charge density at the area non-coincident the at least a partial, part or whole latent fingerprint.

4. A method according to claim 1, comprising applying an electrical potential of the order of 2.5 kV.

5. A method according to claim 1, wherein deploying a detection element further comprises deploying a conductive powder to the surface such that the conductive powder is attracted to the surface coincident the at least a partial, part or whole latent fingerprint.

6. A method according to claim 5, comprising providing a detection element comprising ceramic beads coated in the conductive powder, such that at least a part of the conductive powder is removed from the ceramic beads and is attracted to the surface coincident the at least a partial, part or whole latent fingerprint, thereby providing a visualisation of the latent fingerprint.

7. A method according to claim 5, comprising deploying the conductive powder onto the surface using an aerosol spray, such that the conductive powder is attracted to the surface coincident the at least a partial, part or whole latent fingerprint, thereby providing a visualisation of the latent fingerprint.

8. A method according to claim 7, further comprising charging the aerosol nozzle with a potential.

9. A method according to claim 1, further comprising heating the detection element such that it binds to the surface.

* * * * *